(12) United States Patent
Lakhotia et al.

(10) Patent No.: US 10,197,519 B2
(45) Date of Patent: Feb. 5, 2019

(54) GAS SENSING SYSTEMS AND METHODS

(71) Applicant: H2Scan Corporation, Valencia, CA (US)

(72) Inventors: Vikas Lakhotia, Valencia, CA (US); An Trong Nguyen Le, Stevenson Ranch, CA (US); Timothy Wayne Howard, Canyon Country, CA (US); Matthew Robert Phillipps, Santa Clarita, CA (US)

(73) Assignee: H2Scan Corporation, Valencia, CA (US)

( * ) Notice: Subject to any disclaimer, the term of this patent is extended or adjusted under 35 U.S.C. 154(b) by 241 days.

(21) Appl. No.: 14/208,141

(22) Filed: Mar. 13, 2014

(65) Prior Publication Data

US 2014/0260541 A1 Sep. 18, 2014

Related U.S. Application Data

(60) Provisional application No. 61/788,344, filed on Mar. 15, 2013.

(51) Int. Cl.
*G01N 25/00* (2006.01)
*G01N 27/12* (2006.01)

(52) U.S. Cl.
CPC .................................. *G01N 27/12* (2013.01)

(58) Field of Classification Search
CPC .. G01N 30/30; G01N 30/463; G01N 30/6095; G01N 27/12

(Continued)

(56) References Cited

U.S. PATENT DOCUMENTS 5,507,879 A 4/1996 Gyoten et al.
5,522,225 A 6/1996 Eskandari
(Continued)

FOREIGN PATENT DOCUMENTS

JP 3834633 B2 8/2006

OTHER PUBLICATIONS

Sanjay C. Gadkari, et al., "Solid State Sensors for Toxic Gases," Technical Physics and Prototype Engineering Division, Bhabha Atomic Research Centre, Founder's Day Special Issue, 2006, pp. 49-60.

(Continued)

*Primary Examiner* — Natalie Huls
*Assistant Examiner* — Monica S Young
(74) *Attorney, Agent, or Firm* — Jeffrey G. Sheldon; Katherine B. Sales; Cislo & Thomas LLP

(57) ABSTRACT

An apparatus and method for sensing the amount of a gas in a fluid are disclosed. The apparatus may include a gas sensor, a temperature sensor, a first temperature adjusting unit, or a second temperature adjusting unit. The first and second temperature adjusting units may control the temperature of the gas sensor. The first and second temperature adjusting units may each be used to control the temperature of the gas sensor. According to one technique, they may be used simultaneously to control the temperature of the gas sensor. The temperature sensor may be used to sense the temperature of the gas when it has stabilized to the fluid temperature in which it is being used and the temperature of the gas sensor when it is being controlled by at least one of the first or second temperature adjusting units.

24 Claims, 4 Drawing Sheets

(58) Field of Classification Search
USPC .................................................. 73/25.05
See application file for complete search history.

(56) References Cited

U.S. PATENT DOCUMENTS

| | | | |
|---|---|---|---|
| 5,644,080 A | 7/1997 | Stormbom et al. | |
| 5,689,059 A * | 11/1997 | Oh .................... | G01N 25/28 204/408 |
| 6,073,480 A * | 6/2000 | Gokhfeld ............ | G01N 27/124 73/29.02 |
| 6,450,007 B1 * | 9/2002 | O'Connor ............ | G01N 27/12 338/34 |
| 6,564,633 B2 | 5/2003 | Stormbom | |
| 7,174,768 B2 | 2/2007 | Ito et al. | |
| 7,228,725 B2 | 6/2007 | Salter et al. | |
| 7,249,490 B2 | 7/2007 | Pendergrass | |
| 7,389,672 B2 | 6/2008 | Howard et al. | |
| 7,530,259 B2 | 5/2009 | Tai et al. | |
| 7,565,827 B2 | 7/2009 | Salter et al. | |
| 7,913,542 B2 | 3/2011 | Pedergrass | |
| 8,265,881 B1 | 9/2012 | Lakhotia et al. | |
| 2004/0261526 A1 * | 12/2004 | Poole .................. | G01N 27/223 73/335.06 |
| 2006/0152238 A1 * | 7/2006 | Beaman ............. | G01R 31/2874 324/750.08 |
| 2007/0040702 A1 * | 2/2007 | Mosher ................ | B64G 1/10 340/943 |
| 2009/0126454 A1 * | 5/2009 | Pratt .................. | G01N 33/0059 73/1.02 |
| 2009/0133472 A1 * | 5/2009 | Tada .................... | G01N 27/18 73/31.05 |
| 2009/0301879 A1 | 12/2009 | Soundarrajan et al. | |
| 2010/0210029 A1 * | 8/2010 | Meinhart ............. | G01N 21/05 436/168 |
| 2010/0235107 A1 | 9/2010 | Fukumura et al. | |
| 2010/0332147 A1 * | 12/2010 | Stephens .............. | G01N 33/005 702/24 |
| 2011/0005300 A1 * | 1/2011 | Wang .................. | G01N 30/30 73/23.4 |
| 2011/0163457 A1 * | 7/2011 | Mohan ................ | H01L 21/4853 257/774 |
| 2011/0168557 A1 * | 7/2011 | Park .................... | G01N 27/4074 204/424 |
| 2011/0259081 A1 * | 10/2011 | Chou .................. | G01N 29/022 73/23.42 |
| 2011/0314893 A1 * | 12/2011 | Masui ................ | G01N 27/4067 73/1.06 |
| 2012/0288865 A1 | 11/2012 | Sundberg et al. | |
| 2013/0114082 A1 * | 5/2013 | Sailor ................ | G01N 21/171 356/402 |
| 2015/0075256 A1 * | 3/2015 | Basham ............. | G01N 33/0016 73/31.01 |
| 2015/0084148 A1 * | 3/2015 | Oganesian ......... | H01L 27/14618 257/433 |

OTHER PUBLICATIONS

J. Zosel, et al., "The Measurement of dissolved and gaseious carobn dioxide concentration," Measurement Science Technolology, IOPScience, vol. 22, No. 7, 2011, pp. 1-4.

* cited by examiner

GAS SENSING SYSTEMS AND METHODS

CROSS REFERENCE TO OTHER APPLICATIONS

This application claims priority to U.S. Provisional Patent Application No. 61/788,344 titled "Gas Sensing Systems and Methods" and filed on Mar. 15, 2013. The entire disclosure of U.S. Provisional Patent Application No. 61/788,344 is hereby incorporated by reference.

BACKGROUND

Generally, this application relates to gas sensors. In particular, this application relates to gas sensors used to determine the amount of a gas in a fluid.

Gas sensors may be used to measure the amount of one or more gases in a fluid. The term "amount" should be understood to include concentration or partial pressure. To obtain a measurement, a gas sensor may be at least partially immersed in a fluid. The term "fluid" should be understood to include one or more liquids or gases. Exemplary liquids may include mineral oil, water, or alcohols. Exemplary gases may include hydrogen, oxygen, carbon dioxide, carbon monoxide, or acetylene. One example of a gas sensor may be based on the catalytic dissociation of gas on the surface of a palladium alloy. Molecular species such as gaseous hydrogen or other gases may readily dissociate on the surface of the alloy. The protons from the hydrogen may then be free to dissolve into the matrix of the metal. At low levels of the hydrogen, these dissolved protons may migrate to insulating interfaces and may be detected using, for example, capacitors, diodes, or transistors that shift their physical properties in response to the dipole layer formed by the accumulation of the atomic hydrogen at the interface.

As the hydrogen concentration increases, and as the hydrogen becomes more dissolved into the matrix of the palladium alloy, the resistance of the alloy may increase, and may be detected using resistors or transistors. Not only may the dissolved hydrogen provide scattering sites for the free electrons, but it can also distort the lattice and shift the Fermi levels of the electrons. The net effect may be an increase in resistance that is proportional to the amount of dissolved hydrogen and hence it is proportional to the amount of hydrogen gas above the palladium alloy. Since resistance may also have relatively strong temperature dependence, the temperature of the gas sensor has to be controlled and/or measured to obtain a substantially accurate amount measurement. To obtain a substantially accurate measurement, a gas sensor may be set to a substantially uniform and constant temperature. When a gas sensor is operated at a higher temperature, it may have a faster response time but may be less accurate. When a gas sensor is operated at a lower temperature, it may have a slower response time but may be more sensitive and/or accurate.

A heating device may be used to control the temperature of the gas sensor. However, when only a heating device is used to control the temperature of the gas sensor, the gas sensor must operate at a temperature higher than the temperature of the fluid in which it is at least partially immersed, in order to operate the sensor at a substantially uniform and constant temperature. In that circumstance, the operational temperature of the device is limited to a temperature that is higher than the temperature of the fluid in which the gas sensor is at least partially immersed. The result may be to affect the accuracy and/or sensitivity of the gas sensor. Though turning the heater off allows operation at a lower temperature near the temperature of the fluid in which the gas sensor is at least partially immersed, that often results in poor thermal control and negatively affects the accuracy and/or sensitivity.

In certain types of gas sensors, the solubility of the gas, and hence the sensitivity of the gas sensor, may increase at lower operating temperatures. One such system is a hydrogen sensor with palladium alloys. Operating these types of gas sensors at relatively lower temperatures may allow for relatively higher sensitivity. Additionally, certain drift processes in gas sensors may be thermally related and become pronounced at higher operating temperatures. Lower operating temperatures may allow the gas sensor to remain more accurate over a longer period of time.

Conversely, the response times for certain gas sensors to accurately detect the amount of gas may decrease as temperatures increase, such that operating the gas sensor at higher temperatures may be helpful for the gas sensor to respond relatively quickly to changes in the gas being sensed.

It may be desirable to provide a gas sensor that solves these and other problems.

SUMMARY

An apparatus for sensing the amount of gas in a fluid may include a gas sensor, a temperature sensor, a first temperature adjusting unit, and/or a second temperature adjusting unit. The first temperature adjusting unit and second temperature adjusting unit may be used to control the temperature of the gas sensor. The first temperature adjusting unit may provide heating to the gas sensor. The second temperature adjusting unit may provide heating or cooling to the gas sensor. The first and second temperature adjusting units may be operated simultaneously. The temperature of the gas sensor may be adjusted to a constant predetermined temperature that is substantially uniform throughout the gas sensor. The first temperature adjusting unit may provide relatively fine heating to the gas sensor while the second temperature adjusting unit may provide relatively coarse heating or cooling to the gas sensor. The gas sensor, temperature sensor, and first temperature adjusting unit may be placed on a single die, solid state device or material, or a similar solid state configuration of thermally conductive material.

A controller for controlling an apparatus for sensing the amount of gas in a fluid may include a processor, a first temperature adjusting unit control, a second temperature adjusting unit control, and/or a sensor control. The sensor control may obtain a gas sensor signal from a gas sensor representing the amount of gas in a fluid. The term "signal" should be understood to encompass any data, control information, voltage, current, or power that may be communicated or transferred via electrical conductors. The sensor control may also obtain a temperature sensor signal from a temperature sensor representing the temperature of the gas sensor. The sensor control may communicate the gas sensor signal and temperature sensor signal to the processor which may process them and record data representing those signals in a memory. The processor may control the first temperature adjusting unit control to generate a first temperature adjusting signal to control the first temperature adjusting unit. The processor may also control the second temperature adjusting unit control to generate a second temperature adjusting signal to control the second temperature adjusting unit. The first and second temperature adjusting units may be operated simultaneously.

A method of sensing the amount of gas in a fluid may include detecting the amount of gas in a fluid, measuring the temperature of the gas sensor with a temperature sensor, adjusting the temperature of the gas sensor with a first temperature adjusting unit, and/or adjusting the temperature of the gas sensor with a second temperature adjusting unit. The method may further include allowing the temperature of the gas sensor to stabilize at the fluid temperature, then recording the temperature of the gas sensor, then adjusting and holding the temperature of the gas sensor to a substantially uniform predetermined temperature that is different from the fluid temperature, and/or then detecting and recording the amount of gas in the fluid. The gas sensor may be allowed to remain at the fluid temperature for a first predetermined period of time. The gas sensor may be held at the predetermined temperature for a second predetermined period of time. The second predetermined period of time may be longer than the first predetermined period of time. The second predetermined period of time may not be contemporaneous with the first predetermined period of time. The predetermined temperature may be either higher or lower than the fluid temperature. The first temperature adjusting unit or the second temperature adjusting unit may individually be used to adjust the temperature of the gas sensor. Alternatively, both the first and second temperature adjusting units may be used simultaneously or individually to adjust the temperature of the gas sensor.

Figure 1A:
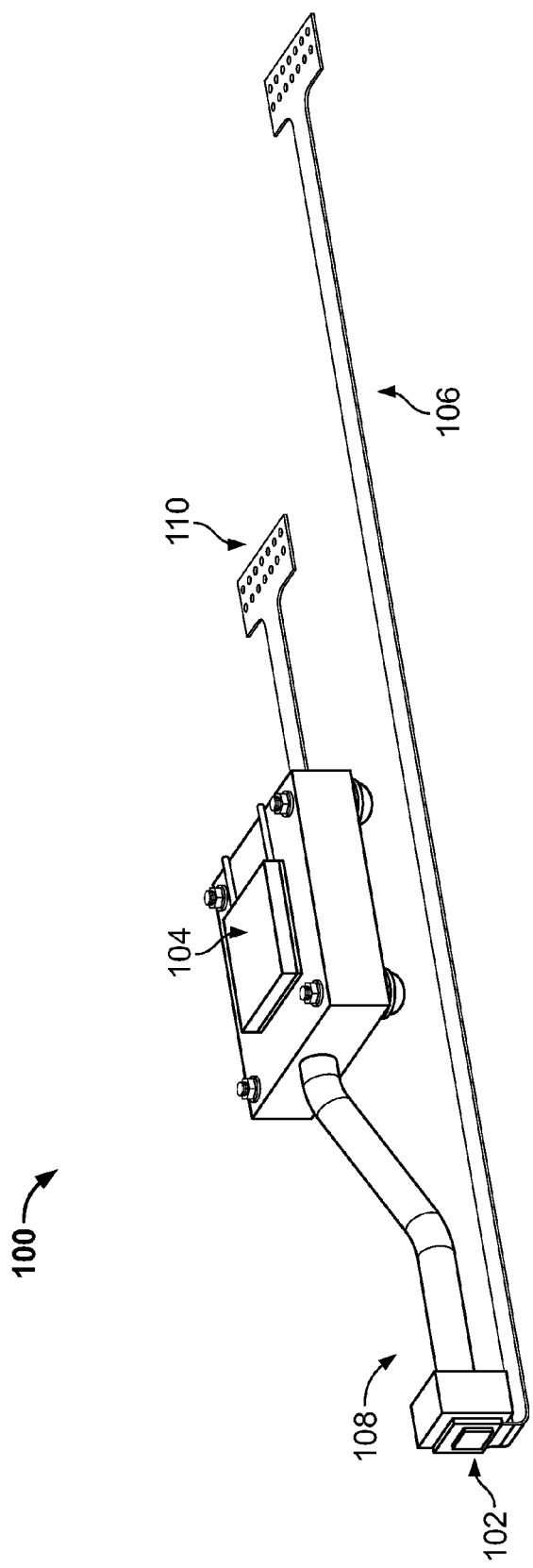
FIG. 1A illustrates an embodiment of a gas sensing subsystem, according to inventive techniques.

The foregoing summary, as well as the following detailed description of certain techniques, will be better understood when read in conjunction with the appended drawings. For the purposes of illustration, certain techniques are shown in the drawings. It should be understood, however, that the claims are not limited to the arrangements and instrumentality shown in the attached drawings.

DETAILED DESCRIPTION

Figure 1B:
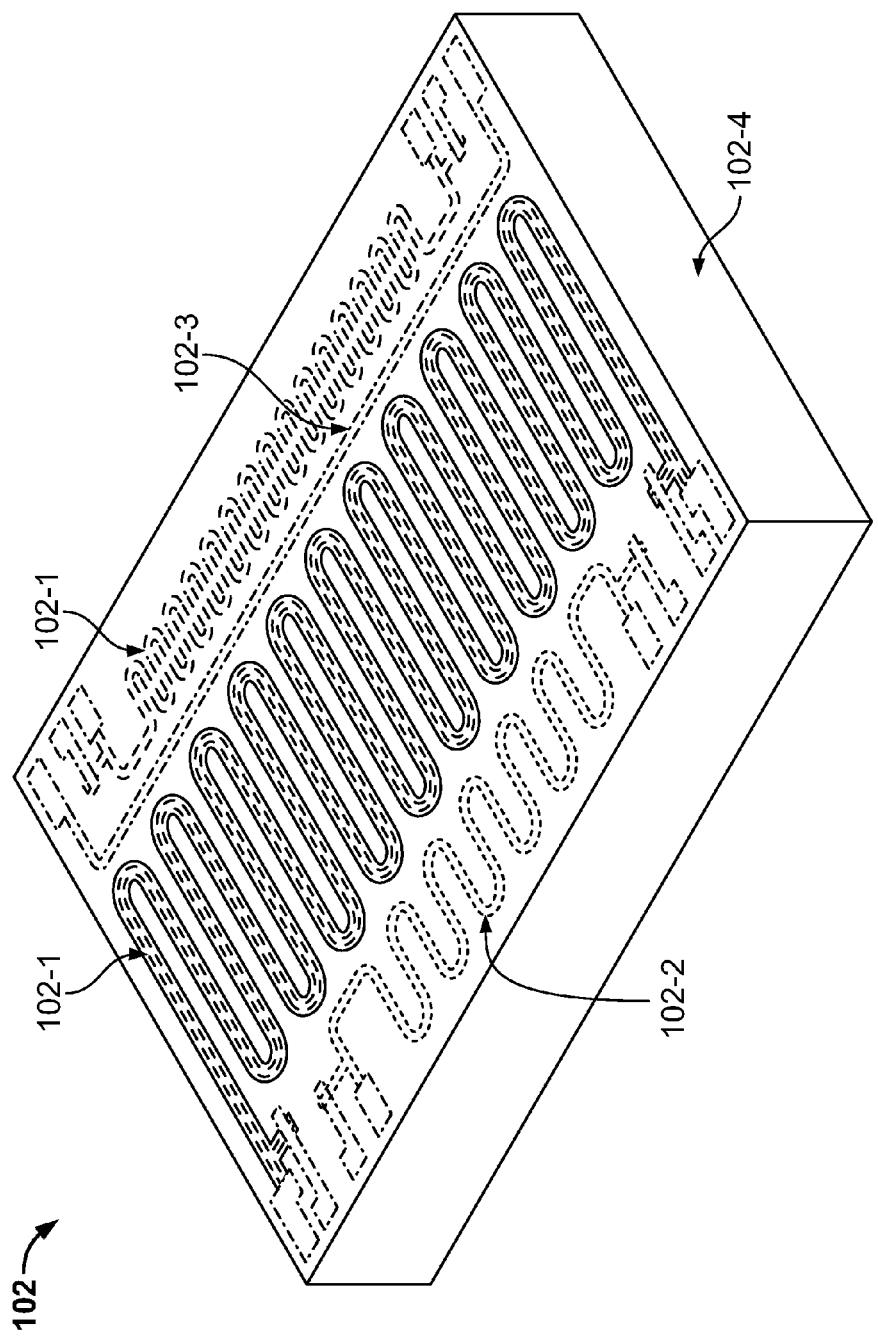
FIG. 1B illustrates an embodiment of a gas sensor subassembly, according to inventive techniques.

FIGS. 1A and 1B illustrate embodiments of a gas sensing subsystem 100 and a gas sensor subassembly 102, respectively, according to certain inventive techniques.

Referring to FIG. 1A, the gas sensing subsystem 100 may include a gas sensor subassembly 102, a second temperature adjusting unit 104, a first electrical connector 106, a thermal connector 108, and/or a second electrical connector 110. As shown in FIG. 1A, the second temperature adjusting unit 104 is separate from the gas sensor subassembly 102. Referring to FIG. 1B, the gas sensor subassembly 102 may include a gas sensor 102-1, a temperature sensor 102-2, and/or a first temperature adjusting unit 102-3.

The gas sensor 102-1 may be thermally coupled to the second temperature adjusting unit 104 with a thermal connector 108. The gas sensor 102-1 may be thermally coupled to the first temperature adjusting unit 102-3. The gas sensor 102-1 may be electrically coupled to the first electrical connector 106. The temperature sensor 102-2 may be electrically coupled to the first electrical connector 106. The first temperature adjusting unit 102-3 may be electrically coupled to the first electrical connector 106. The second temperature adjusting unit 104 may be electrically coupled to the second electrical connector 110.

In operation, the gas sensor 102-1 may be adapted to sense the amount of a gas in a fluid when the gas sensor 102-1 is at least partially immersed in the fluid. Examples of gases detected include hydrogen, oxygen, carbon dioxide, carbon monoxide, acetylene, or water vapor. The temperature sensor 102-2 may be adapted to sense the temperature of the gas sensor 102-1. The first temperature adjusting unit 102-3 may be adapted to adjust the temperature of the gas sensor 102-1. The second temperature adjusting unit 104 may be adapted to adjust the temperature of the gas sensor 102-1.

The gas sensor 102-1 may be held at a substantially constant predetermined temperature that is substantially uniform throughout the gas sensor 102-1 to measure the amount of a gas in fluid. The gas sensor 102-1 may include materials that are sensitive to the presence of the specific gas being detected. Examples of some materials that could be used for a hydrogen gas sensor may include palladium, platinum, iridium, nickel, their alloys, or metal oxide such as tungsten oxide. The gas sensor 102-1 may include a resistor, capacitor, transistor, or diode.

The temperature sensor 102-2 may be proximate to the gas sensor 102-1 to measure the temperature of the gas sensor 102-1 with substantial accuracy. For example, the temperature sensor 102-2 and the gas sensor 102-1 may be placed approximately 0.05 inches apart from one another. When the temperature sensor 102-2 and the gas sensor 102-1 are placed in close proximity to one another, the temperature difference between the two elements may be as low as 0.005 degrees Celsius. The temperature sensor 102-2 may include a resistor, capacitor, thermocouple, or diode. The temperature sensor 102-2 may provide an accurate and/or sensitive measurement of the temperature of the fluid or the gas sensor 102-1 by measuring the change in, for example, the resistance or capacitance of the temperature sensor 102-2 and correlating that change to previously established calibration curves.

The first temperature adjusting unit 102-3 may be proximate to the gas sensor 102-1 to adjust the temperature of the gas sensor 102-1 with substantial accuracy. For example, the first temperature adjusting unit 102-3 may be placed approximately 0.05 inches from the gas sensor 102-1. When the first temperature adjusting unit 102-3 and the gas sensor 102-1 are placed in close proximity to one another, the temperature difference between them may be as low as 0.005 degrees Celsius. The first temperature adjusting unit 102-3 may include a heater (for example, a resistive heating element). The first temperature adjusting unit 102-3 may be further adapted to receive a first temperature adjusting signal via the first electrical connector 106 that controls the operation of the first temperature adjusting unit 102-3. The first temperature adjusting unit 102-3 may be enabled, adjusted, disabled, and/or turned off by the first temperature adjusting signal.

The second temperature adjusting unit 104 may adjust the temperature of the gas sensor 102-1 via the thermal connector 108. Optionally, the second temperature adjusting unit 104 may be located substantially proximate to the gas sensor 102-1 without the interposed thermal connector 108. The second temperature adjusting unit 104 may include a cooler and/or a heater. Such a cooler may include active or passive cooling components. An example of a passive cooling component may be a heat sink. Examples of active cooling components include a thermoelectric cooling device, a refrigerator, or a fan. The second temperature adjusting unit 104 may include a thermoelectric cooler and/or heater that operate according to the Peltier effect. A thermoelectric cooler using the Peltier effect may operate by transferring heat from one side of the thermoelectric cooler to the other side, depending on the potential difference created across the two sides of the thermoelectric cooler. The potential difference may cause electrical current to flow through the thermoelectric cooler, or a voltage difference across the two sides of the thermoelectric cooler, causing one side to heat while the other side cools. Depending on the polarity of the potential difference applied across the thermoelectric cooler, the thermoelectric cooler can be used to provide heating or cooling. The second temperature adjusting unit 104 may be further adapted to receive a second temperature adjusting signal via the second electrical connector 110 that controls the operation of the second temperature adjusting unit 104. The second temperature adjusting unit 104 may be enabled, adjusted, disabled, and/or turned off by the second temperature adjusting signal.

The first temperature adjusting unit 102-3 may be closely integrated with the gas sensor 102-1 through certain semiconductor processing methods. This close integration may allow for fine thermal control of the gas sensor 102-1 by the first temperature adjusting unit 102-3. The second temperature adjusting unit 104 may be a more complex device, such as a Peltier device attached to a heat pipe, that is not as easily integrated with the gas sensor 102-1. The connection between the second temperature adjusting unit 104 and the gas sensor 102-1 may only allow coarse thermal control.

The ability to control the gas sensor to both low and high temperatures may allow the performance of the gas sensor to be optimized for different environments. For instance, the operating temperature could be lowered to optimize stability and sensitivity when conditions are detected to be fairly static. The operating temperature could then be elevated to higher temperatures when conditions are changing rapidly so that the gas sensor can respond quickly to the changes.

As shown in FIG. 1A, the thermal connector 108 may include a heat exchanger such as a heat pipe adapted to transfer thermal energy between the second temperature adjusting unit 104 and the gas sensor 102-1. The heat pipe is for directly controlling the temperature of the gas sensor.

The first electrical connector 106 may include a flex cable. The second electrical connector 110 may include a flex cable.

The first temperature adjusting unit 102-3 may be used to adjust and hold the temperature of the gas sensor 102-1 to a predetermined temperature. The first temperature adjusting unit 102-3 may be adapted to receive a first temperature adjusting signal via the first electrical connector 106 and may adjust the temperature of the gas sensor 102-1 according to the first temperature adjusting signal. The second temperature adjusting unit 104 may be used to adjust and hold the temperature the gas sensor 102-1 to a predetermined temperature. The second temperature adjusting unit 104 may be adapted to receive a second temperature adjusting signal via the second electrical connector 110 and may adjust the temperature of the gas sensor 102-1 according to the second temperature adjusting signal. Both the first temperature adjusting unit 102-3 and the second temperature adjusting unit 104 may be used, either simultaneously or individually, to adjust and hold the temperature of the gas sensor 102-1 to a predetermined temperature. When both the first temperature adjusting unit 102-3 and the second temperature adjusting unit 104 are used, the first temperature adjusting unit 102-3 may adjust the temperature of the gas sensor 102-1 in response to the first temperature adjusting signal received through the first electrical connector 106, and the second temperature adjusting unit 104 may adjust the temperature of the gas sensor 102-1 in response to the second temperature adjusting signal received through the second electrical connector 110.

The second temperature adjusting unit 104 may be used to provide relatively coarse heating or cooling to the gas sensor 102-1. The second temperature adjusting unit 104 may heat or cool the gas sensor 102-1 with an accuracy having an order of magnitude of ones of degrees Celsius (for example, an accuracy of approximately 4 degrees Celsius). The first temperature adjusting unit 102-3 may be used to provide relatively fine heating to the gas sensor 102-1. The first temperature adjusting unit 102-3 may heat the gas sensor 102-1 with an accuracy having an order of magnitude of a hundredth of a degree Celsius (for example an accuracy of approximately 0.01 degree Celsius).

The gas sensor subassembly 102 may further include a thermally conductive material 102-4. The gas sensor 102-1 may be placed on a die, or solid state device or material, including the thermally conductive material 102-4. The temperature sensor 102-2 may be placed on the die, or solid state device or material, including thermally conductive material 102-4. The first temperature adjusting unit 102-3 may be placed on the die or solid state device or material, including thermally conductive material 102-4. The thermally conductive material 102-4 may include silicon, gallium arsenide, gallium nitride, or silicon on insulator (SOI).

Figure 2:
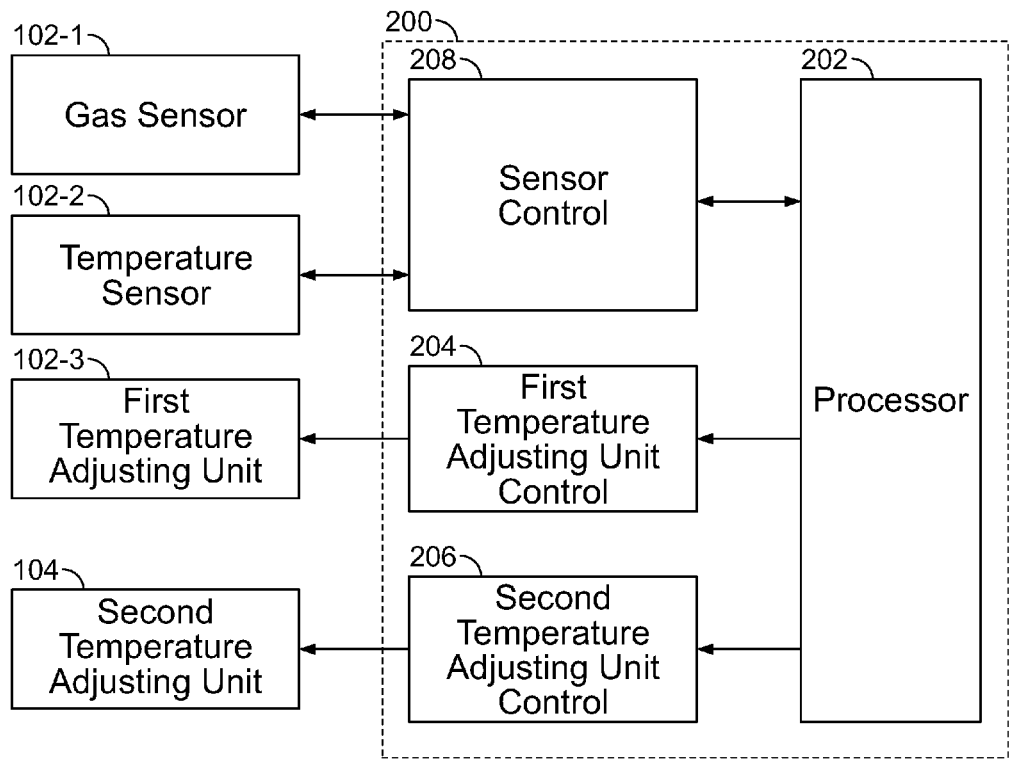
FIG. 2 illustrates a block diagram of a controller and a gas sensing subsystem, according to inventive techniques.

FIG. 2 illustrates a block diagram of a controller 200 and a gas sensing subsystem 100, substantially as described above, according to certain inventive techniques. The controller 200 may be used to control the gas sensing subsystem 100.

The controller 200 may include a processor 202, a first temperature adjusting unit control 204, a second temperature adjusting unit control 206, and/or a sensor control 208. Although not shown, the controller 200 may also include memory, a display, networks and/or network drivers and I/Os, and/or user interface components.

The processor 202 may be electrically coupled to the first temperature adjusting unit control 204, the second temperature adjusting unit control 206, and/or the sensor control 208. The first temperature adjusting unit control 204 may be electrically coupled to the first temperature adjusting unit 102-3. The second temperature adjusting unit control 206 may be electrically coupled to the second temperature adjusting unit 104. The sensor control 208 may be electrically coupled to the gas sensor 102-1 or the temperature sensor 102-2.

The first temperature adjusting unit control 204 may include a current or voltage source that controls the amount of current or voltage provided to the first temperature adjusting unit 102-3. The second temperature adjusting unit control 206 may include a voltage source that controls the amount or polarity of voltage provided to the second temperature adjusting unit 104. As described above, the polarity of the voltage provided to the second temperature adjusting unit 104 may affect whether the second temperature adjusting unit 104 provides heating or cooling to the gas sensor 102-1 when the second temperature adjusting unit 104 is a thermoelectric cooler that operates using the Peltier effect. The sensor control 208 may include two current or voltage sources. One current or voltage source may provide current to the gas sensor 102-1, which may include at least one resistor, capacitor, transistor, or diode. By providing current or voltage to the gas sensor 102-1, a change in resistance, capacitance, or conductance of the gas sensor 102-1 (which is proportional to the amount of the gas being sensed as described above) can be determined. One current or voltage source may be used to provide current or voltage to the temperature sensor 102-2, which may include at least one resistor, capacitor, transistor, or diode. By providing current or voltage to the temperature sensor 102-2, a change in resistance, capacitance, or conductance of the temperature sensor 102-2 (which is proportional to the temperature of the gas sensor) can be determined.

In operation, a gas sensor signal that represents an amount of a gas in a fluid may be obtained by the sensor control 208 from the gas sensor 102-1. The gas sensor 102-1 may include a resistor, capacitor, transistor, or diode with known resistance, capacitance, or conductance. By providing current or voltage to the gas sensor 102-1, a change in resistance, capacitance, or conductance of the gas sensor 102-1 (which is proportional to the amount of the gas being sensed as described above) may be determined by measuring the change in voltage across the gas sensor 102-1. The change in voltage across the gas sensor 102-1 can be used to determine the amount of gas in the fluid.

A temperature sensor signal that represents the temperature of the gas sensor 102-1 may be obtained by the sensor control 208 from the temperature sensor 102-2. The temperature sensor 102-2 may include a resistor, capacitor, diode, or transistor with known resistance, capacitance, or conductance. By providing current or voltage to the temperature sensor 102-2, a change in resistance, capacitance, or conductance of the temperature sensor 102-2 can be determined by measuring the change in voltage across the temperature sensor 102-2. The change in voltage across the temperature sensor 102-2 may be used to determine the temperature.

The sensor control 208 may be further adapted to transmit the gas sensor signal and the temperature sensor signal to the processor 202, and the processor 202 may be adapted to receive the gas sensor signal and the temperature sensor signal. The processor 202 may then process the gas sensor signal and record data representing the gas sensor signal in memory (for example, volatile or nonvolatile memory). The first temperature adjusting unit control 204 may be adapted to be controlled by the processor 202, and may be adapted to generate a first temperature adjusting signal to control the first temperature adjusting unit 102-3. The second temperature adjusting unit control 206 may be adapted to be controlled by the processor 202 and may be adapted to generate a second temperature adjusting signal to control the second temperature adjusting unit 104.

The first temperature adjusting signal may be generated by the first temperature adjusting unit control 204 based on control by the processor 202. The first temperature adjusting signal may be used to enable, adjust, disable, and/or turn off the first temperature adjusting unit 102-3. The second temperature adjusting signal may be generated by the second temperature adjusting unit control 206 based on control by the processor 202. The second temperature adjusting signal may be used to enable, adjust, disable, and/or turn off the second temperature adjusting unit 104.

To allow the temperature of the gas sensor 102-1 to stabilize at the temperature of the fluid in which the gas sensor 102-1 has been immersed, the first temperature adjusting signal may be used to disable or turn off the first temperature adjusting unit 102-3 and the second temperature adjusting signal may be used to disable or turn off the second temperature adjusting unit 104. When the temperature of the gas sensor 102-1 has stabilized at the temperature of the fluid, the sensor control 208 may obtain the temperature sensor signal from the temperature sensor 102-2 representing the temperature of the gas sensor 102-1 and may transmit the temperature sensor signal to the processor 202 which processes it and records data representing the temperature sensor signal in memory (for example, volatile or nonvolatile memory). The temperature sensor signal may be processed or filtered by the sensor control 208 before it is transmitted to the processor 202.

After the processor 202 has received the temperature sensor signal after the temperature of the gas sensor 102-1 has stabilized at the fluid temperature in which the gas sensor 102-1 has been at least partially immersed, the processor 202 may control the first temperature adjusting unit control 204 to generate a first temperature adjusting signal for the first temperature adjusting unit 102-3 to adjust the temperature of the gas sensor 102-1 to a substantially uniform predetermined temperature that is higher than the fluid temperature. After the first temperature adjusting unit 102-3 has adjusted the temperature of the gas sensor 102-1 to the predetermined temperature, the sensor control 208 may obtain a gas sensor signal from the gas sensor 102-1 representing the amount of the gas in the fluid.

After the processor 202 has received the temperature sensor signal after the temperature of the gas sensor 102-1 has stabilized at the fluid temperature in which the gas sensor 102-1 has been at least partially immersed, the processor 202 may control the second temperature adjusting unit control 206 to generate a second temperature adjusting signal for the second temperature adjusting unit 104 to adjust the temperature of the gas sensor 102-1 to a substantially uniform predetermined temperature that is higher than the fluid temperature. After the second temperature adjusting unit 104 has adjusted the temperature of the gas sensor 102-1 to the predetermined temperature, the sensor control 208 may obtain a gas sensor signal from the gas sensor 102-1 representing the amount of the gas in the fluid.

After the processor 202 has received the temperature sensor signal after the temperature of the gas sensor 102-1 has stabilized at the fluid temperature in which the gas sensor 102-1 has been at least partially immersed, the processor 202 may control the first temperature adjusting unit control 204 to generate a first temperature adjusting signal for the first temperature adjusting unit 102-3 and may control the second temperature adjusting unit control 206 to generate a second temperature adjusting signal for the second temperature adjusting unit 104, to adjust the temperature of the gas sensor 102-1 to a substantially uniform predetermined temperature that is higher than the fluid temperature. After the first temperature adjusting unit 102-3 and the second temperature adjusting unit 104 have adjusted the temperature of the gas sensor 102-1 to the predetermined temperature, the sensor control 208 may obtain a gas sensor signal from the gas sensor 102-1 representing the amount of the gas in the fluid. The first temperature adjusting unit 102-3 and the second temperature adjusting unit 104 may adjust the temperature of the gas sensor 102-1 simultaneously.

After the processor 202 has received the temperature sensor signal after the temperature of the gas sensor 102-1 has stabilized at the fluid temperature in which the gas sensor 102-1 has been at least partially immersed, the processor 202 may control the second temperature adjusting unit control 206 to generate a second temperature adjusting signal for the second temperature adjusting unit 104 to adjust the temperature of the gas sensor 102-1 to a substantially uniform predetermined temperature that is lower than the fluid temperature. After the second temperature adjusting unit 104 has adjusted the temperature of the gas sensor 102-1 to the predetermined temperature, the sensor control 208 may obtain a gas sensor signal from the gas sensor 102-1 representing the amount of the gas in the fluid.

After the processor 202 has received the temperature sensor signal after the temperature of the gas sensor 102-1 has stabilized at the fluid temperature in which the gas sensor 102-1 is being used, the processor 202 may control the first temperature adjusting unit control 204 to generate a first temperature adjusting signal for the first temperature adjusting unit 102-3 and may control the second temperature adjusting unit control 206 to generate a second temperature adjusting signal for the second temperature adjusting unit 104, to adjust the temperature of the gas sensor 102-1 to a substantially uniform predetermined temperature that is lower than the fluid temperature. After the first temperature adjusting unit 102-3 and the second temperature adjusting unit 104 have adjusted the temperature of the gas sensor 102-1 to the predetermined temperature, the sensor control 208 may obtain a gas sensor signal from the gas sensor 102-1 representing the amount of the gas in the fluid. The first temperature adjusting unit 102-3 and the second temperature adjusting unit 104 may adjust the temperature of the gas sensor 102-1 simultaneously.

The gas sensor subassembly 102 may include two gas sensors (for example, similar to the gas sensor 102-1 in FIG. 1B). Each gas sensor may be controlled by a different sensor control (for example, similar to the sensor control 208 in FIG. 2). Alternatively, the two gas sensors may be controlled by a single sensor control (for example, similar to the sensor control 208 in FIG. 2). The two gas sensors may each have a separate first temperature adjusting unit (for example, similar to the first temperature adjusting unit 102-3 in FIG. 1B) adapted to provide heating to each gas sensor. Alternatively, the two gas sensors may be controlled by a single first temperature adjusting unit (for example, similar to the first temperature adjusting unit 102-3 in FIG. 1B) adapted to provide heating to both gas sensors. A separate temperature sensor (for example, similar to the temperature sensor 102-2 in FIG. 1B) may be used to sense the temperature of each gas sensor. Alternatively, a single temperature sensor (for example, similar to the temperature sensor 102-2 in FIG. 1B) may be used to sense the temperature of both gas sensors. The two gas sensors may each have a separate second temperature adjusting unit (for example, similar to the second temperature adjusting unit 104 in FIGS. 1A and 1B) adapted to provide heating or cooling to each gas sensor. Alternatively, the two gas sensors may be controlled by a single second temperature adjusting unit (for example, similar to the second temperature adjusting unit 104 in FIGS. 1A and 1B) adapted to provide heating or cooling to both gas sensors. Both gas sensors may be at least partially immersed in a fluid to detect an amount of gas in the fluid.

Figure 3:
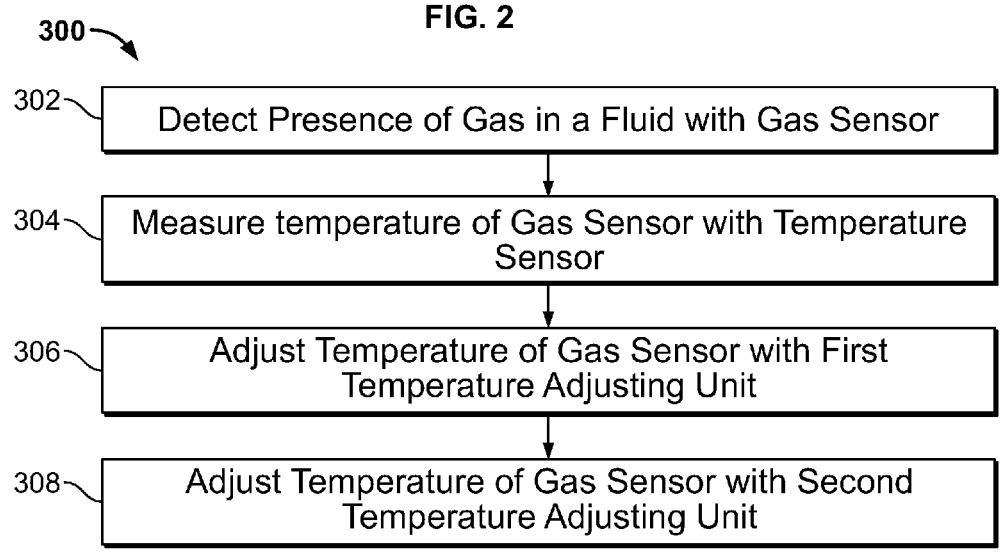
FIG. 3 shows a flowchart for a method of sensing the amount of a gas in a fluid, according to inventive techniques.

FIG. 3 shows a flowchart 300 for a method of sensing the amount of a gas in a fluid, according to certain inventive techniques. The flowchart is shown to have various steps. Some steps may be omitted, and/or may be performed in a different order. The method may be performed with a gas sensing subsystem 100, gas sensor subassembly 102, and controller 200 substantially as described above.

At 302, a gas sensor may be used to detect the amount of gas in a fluid. The gas sensor may be placed on a single die, or solid state device or material, made of a thermally conductive material such as silicon.

At 304, a temperature sensor may be used to detect the temperature of the gas sensor. The temperature sensor may be placed on the single die, or solid state device or material, made on a thermally conductive material such as silicon that includes a gas sensor.

At 306, a first temperature adjusting unit may be used to adjust the temperature of the gas sensor. The first temperature adjusting unit may be placed on a single die, or solid state device or material, made of thermally conductive material, such as silicon, that includes a gas sensor and a temperature sensor. The first temperature adjusting unit may be a heater. The first temperature adjusting unit may be a resistor, transistor, or diode. The first temperature adjusting unit may be controlled by a controller. The controller may include a current or voltage source that generates current or voltage for the first temperature adjusting unit. In another embodiment, the first temperature adjusting unit may be used to provide fine heating to the gas sensor.

At 308, a second temperature adjusting unit may be used to adjust the temperature of the gas sensor. The second temperature adjusting unit may be a heater. The second temperature adjusting unit may be a cooler. The second temperature adjusting unit may be a Peltier effect thermoelectric cooler. The second temperature adjusting unit may be a heat sink. The second temperature adjusting unit may be a compressor. The second temperature adjusting unit may be controlled by a controller. The controller may include a voltage or current source that drives the second temperature adjusting unit. The first temperature adjusting unit and the second temperature adjusting unit may both be used to adjust the temperature of the gas sensor. The first temperature adjusting unit and the second temperature adjusting unit may be used simultaneously to adjust the temperature of the gas sensor. The second temperature adjusting device may be used to provide coarse cooling to the gas sensor. The second temperature adjusting device may be used to provide coarse heating to the gas sensor.

Figure 4:
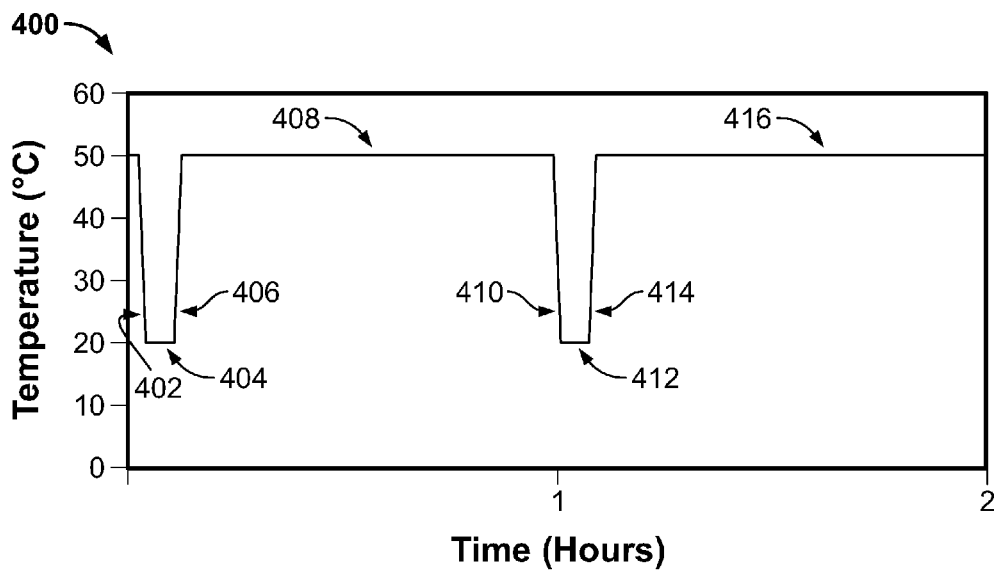
FIGS. 4 and 5 show charts illustrating methods for sensing the amount of a gas in a fluid, according to inventive techniques.

FIG. 4 is a graph 400 representing one method for sensing the amount of gas in a fluid. The method may be performed with a gas sensing subsystem 100, gas sensor subassembly 102, and controller 200 substantially as described above. The units provided in FIG. 4 are for illustrative purposes only and are not intended to limit the invention in any way.

At 402, the temperature of the gas sensor may be allowed to stabilize at the fluid temperature in which the gas sensor is at least partially immersed. This may be done by disabling both the first temperature adjusting unit and the second temperature adjusting unit. Alternatively, the second temperature adjusting unit may be used to provide cooling to the gas sensor to speed up this part of the process. In this embodiment, the fluid temperature is lower than a predetermined temperature of the gas sensor. Knowing the temperature of the fluid may be helpful to make the gas sensor readings comparable to reference or industry standards. In one case, knowing the ambient fluid temperature would allow a water vapor measurement to be expressed in terms of relative saturation (RS %) of the fluid for the current temperature. In another case, the fluid temperature would allow a measurement of dissolved gases in liquids to be comparable to the results from the lab Dissolved Gas Analysis (DGA).

At 404, after the temperature of the gas sensor has stabilized at the fluid temperature, the temperature sensor may be used to record the temperature of the gas sensor. The gas sensor may be allowed to remain at the fluid temperature for a predetermined period of time while the temperature sensor may be used to record the temperature of the gas sensor.

At 406, the temperature of the gas sensor may be adjusted to a predetermined temperature that is greater than the temperature of the fluid. The temperature of the gas sensor may be adjusted using the first temperature adjusting unit. The temperature of the gas sensor may be adjusted using the second temperature adjusting unit. The temperature of the gas sensor may be adjusted using both the first temperature adjusting unit and the second temperature adjusting unit. The temperature of the gas sensor may be adjusted using both the first temperature adjusting unit and the second temperature adjusting unit simultaneously.

At 408, after the temperature of the gas sensor has been adjusted to the predetermined temperature, the gas sensor may detect the amount of a gas in the fluid. The gas sensor may be kept at the predetermined temperature for a predetermined period of time for detecting the amount of gas in the fluid. The predetermined period of time for detecting the amount of gas in the fluid may be longer than the predetermined period of time described at 404. These predetermined periods of time are selected based on the time constant of the temperature sensor and the time constant of the gas sensor. For example, the predetermined period of time described at 404 may be five minutes while the predetermined period of time described at 408 may be 55 minutes. The first temperature adjusting unit may be used to maintain the temperature of the gas sensor at the predetermined temperature. The second temperature adjusting unit may be used to maintain the temperature of the gas sensor at the predetermined temperature. Both the first temperature adjusting unit and the second temperature adjusting unit may be used to maintain the temperature of the gas sensor at the predetermined temperature. Both the first temperature adjusting unit and the second temperature adjusting unit may be used simultaneously to maintain the temperature of the gas sensor at the predetermined temperature.

At 410, the temperature of the gas sensor is allowed to stabilize at the fluid temperature in which the gas sensor is at least partially immersed. This may be done by disabling or turning off both the first temperature adjusting unit and the second temperature adjusting unit. The second temperature adjusting unit 104 may be used to provide cooling to the gas sensor 102-1 to speed up this part of the process.

At 412, after the temperature of the gas sensor has stabilized at the fluid temperature, the temperature sensor may be used to record the temperature of the gas sensor. The gas sensor may be allowed to remain at the fluid temperature for a predetermined period of time while the temperature sensor is used to record the temperature of the gas sensor.

At 414, the temperature of the gas sensor is adjusted to a predetermined temperature that is greater than the temperature of the fluid. The temperature of the gas sensor may be adjusted using the first temperature adjusting unit. The temperature of the gas sensor may be adjusted using the second temperature adjusting unit. The temperature of the gas sensor may be adjusted using both the first temperature adjusting unit and the second temperature adjusting unit. The temperature of the gas sensor may be adjusted using both the first temperature adjusting unit and the second temperature adjusting unit simultaneously.

At 416, after the temperature of the gas sensor has been adjusted to the predetermined temperature, the gas sensor may detect the amount of a gas in the fluid. The gas sensor may be kept at the predetermined temperature for a predetermined period of time for detecting the amount of gas in the fluid. The predetermined period of time for detecting the amount of gas in the fluid may be longer than the predetermined period of time described at 404 and 412. The first temperature adjusting unit may be used to maintain the temperature of the gas sensor at the predetermined temperature. The second temperature adjusting unit may be used to maintain the temperature of the gas sensor at the predetermined temperature. Both the first temperature adjusting unit and the second temperature adjusting unit may be used to maintain the temperature of the gas sensor at the predetermined temperature. Both the first temperature adjusting unit and the second temperature adjusting unit may be used simultaneously to maintain the temperature of the gas sensor at the predetermined temperature.

The method including 402-404-406-408 may be repeated as many times as desired.

Figure 5:
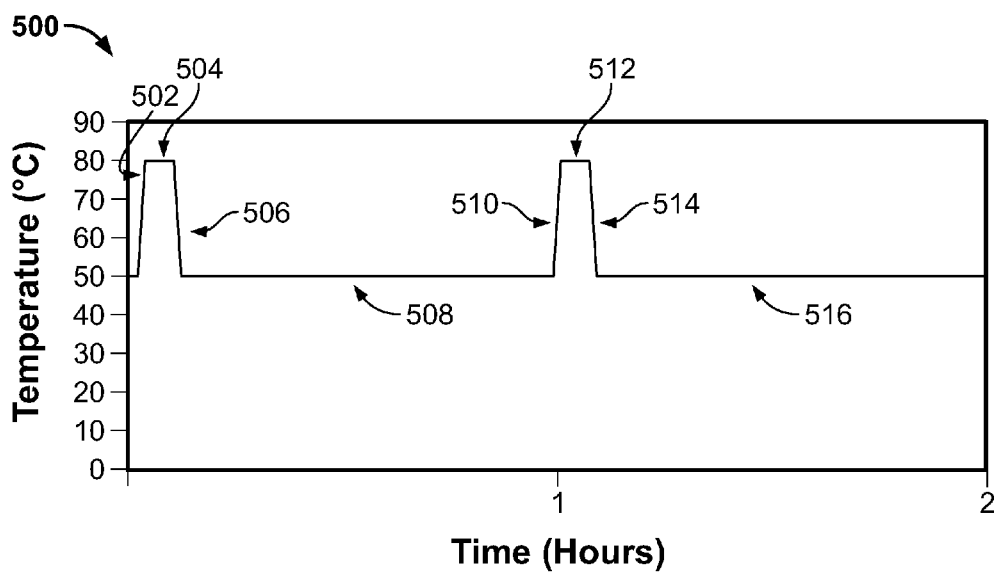

FIG. 5 is a graph 500 representing another method for sensing the amount of gas in a fluid. The method may be performed with a gas sensing subsystem 100, gas sensor subassembly 102, or controller 200 substantially as described above. The units provided in FIG. 5 are for illustrative purposes only and are not intended to limit the invention in any way.

At 502, the temperature of the gas sensor may be allowed to stabilize at the fluid temperature in which the gas sensor is at least partially immersed. This may be done by disabling or turning off both the first temperature adjusting unit and the second temperature adjusting unit. In this embodiment, the fluid temperature is higher than a predetermined temperature of the gas sensor. The first temperature adjusting unit 102-3 may be used to provide heating to the gas sensor 102-1 to speed up this part of the process. The second temperature adjusting unit 104 may be used to provide heating to the gas sensor 102-1 to speed up this part of the process. The first temperature adjusting unit 102-3 and the second temperature adjusting unit 104 both may be used to provide heating to the gas sensor 102-1 to speed up this part of the process. The first temperature adjusting unit 102-3 and the second temperature adjusting unit 104 both may be used simultaneously to provide heating to the gas sensor 102-1 to speed up this part of the process.

At 504, after the temperature of the gas sensor has stabilized at the fluid temperature, the temperature sensor may be used to record the temperature of the gas sensor. The gas sensor may be allowed to remain at the fluid temperature for a predetermined period of time while the temperature sensor is used to record the temperature of the gas sensor.

At 506, the temperature of the gas sensor may be adjusted to a predetermined temperature that is lower than the temperature of the fluid. The temperature of the gas sensor may be adjusted using the second temperature adjusting unit. The temperature of the gas sensor may be adjusted using both the first temperature adjusting unit and the second temperature adjusting unit. The temperature of the gas sensor may be adjusted using both the first temperature adjusting unit and the second temperature adjusting unit simultaneously.

At 508, after the temperature of the gas sensor has been adjusted to the predetermined temperature, the gas sensor may detect the amount of a gas in the fluid. The gas sensor may be kept at the predetermined temperature for a predetermined period of time for detecting the amount of gas in the fluid. The predetermined period of time for detecting the amount of gas in the fluid may be longer than the predetermined period of time described at 504. For example, the predetermined period of time described at 504 may be five minutes while the predetermined period of time described at 508 may be 55 minutes. The second temperature adjusting unit may be used to maintain the temperature of the gas sensor at the predetermined temperature. Both the first temperature adjusting unit and the second temperature adjusting unit may be used to maintain the temperature of the gas sensor at the predetermined temperature. Both the first temperature adjusting unit and the second temperature adjusting unit may be used simultaneously to maintain the temperature of the gas sensor at the predetermined temperature.

At 510, the temperature of the gas sensor may be allowed to stabilize at the fluid temperature in which the gas sensor is at least partially immersed. This may be done by disabling both the first temperature adjusting unit and the second temperature adjusting unit. The first temperature adjusting unit 102-3 may be used to provide heating to the gas sensor 102-1 to speed up this part of the process. The second temperature adjusting unit 104 may be used to provide heating to the gas sensor 102-1 to speed up this part of the process. The first temperature adjusting unit 102-3 and the second temperature adjusting unit 104 both may be used to provide heating to the gas sensor 102-1 to speed up this part of the process. The first temperature adjusting unit 102-3 and the second temperature adjusting unit 104 both may be used simultaneously to provide heating to the gas sensor 102-1 to speed up this part of the process.

At 512, after the temperature of the gas sensor has stabilized at the fluid temperature, the temperature sensor may be used to record the temperature of the gas sensor. The gas sensor may be allowed to remain at the fluid temperature for a predetermined period of time while the temperature sensor is used to record the temperature of the gas sensor.

At 514, the temperature of the gas sensor may be adjusted to a predetermined temperature that is lower than the temperature of the fluid. The temperature of the gas sensor may be adjusted using the second temperature adjusting unit. The temperature of the gas sensor may be adjusted using both the first temperature adjusting unit and the second temperature adjusting unit. The temperature of the gas sensor may be adjusted using both the first temperature adjusting unit and the second temperature adjusting unit simultaneously.

At 516, after the temperature of the gas sensor has been adjusted to the predetermined temperature, the gas sensor may detect the amount of a gas in the fluid. The gas sensor may be kept at the predetermined temperature for a predetermined period of time for detecting the amount of gas in the fluid. The predetermined period of time for detecting the amount of gas in the fluid may be longer than the predetermined period of time described at 504 and 512. The second temperature adjusting unit may be used to maintain the temperature of the gas sensor at the predetermined temperature. Both the first temperature adjusting unit and the second temperature adjusting unit may be used to maintain the temperature of the gas sensor at the predetermined temperature. Both the first temperature adjusting unit and the second temperature adjusting unit may be used simultaneously to maintain the temperature of the gas sensor at the predetermined temperature.

The method including 502-504-506-508 may be repeated as many times as desired.

The ability to control the gas sensor to both low and high temperatures may allow the performance of the gas sensor to be optimized for different environments. For instance, the operating temperature could be lowered to optimize stability and sensitivity when conditions are detected to be fairly static. The operating temperature could then be elevated to higher temperatures when conditions are changing rapidly so that the gas sensor can respond quickly to the changes.

It will be understood by those skilled in the art that various changes may be made and equivalents may be substituted without departing from the scope of the novel techniques disclosed in this application. In addition, many modifications may be made to adapt a particular situation or material to the teachings of the novel techniques without departing from its scope. Therefore, it is intended that the novel techniques not be limited to the particular techniques disclosed, but that they will include all techniques falling within the scope of the appended claims.

What is claimed is:

1. A method of using an apparatus suitable for determining an amount of a gas in a fluid, the apparatus comprising:
    a) a gas sensor subassembly comprising a thermally conductive solid state material, the gas sensor subassembly having on the solid state material:
        i) a gas sensor adapted to sense an amount of a gas in a fluid when the gas sensor has a substantially uniform temperature;
        ii) a temperature sensor proximate to and coupled to the gas sensor for sensing the temperature of the gas sensor; and
        iii) a first temperature adjusting unit coupled to the gas sensor and adapted to adjust the temperature of the gas sensor only by heating;
    b) a second temperature adjusting unit located external to the gas sensor subassembly and adapted to adjust the temperature of the gas sensor by both heating and cooling; and
    c) a heat pipe coupling the second temperature adjusting unit to the gas sensor for directly controlling the temperature of the gas sensor;
    wherein the method comprises the steps of:
    i) detecting the temperature of the gas sensor with the temperature sensor;
    ii) heating the gas sensor with the first temperature adjusting unit, the second temperature adjusting unit, or both the first and second temperature adjusting units when the detected temperature is below a predetermined temperature;
    and
    iii) if the temperature of the gas sensor is above the predetermined temperature, cooling the gas sensor with the second temperature adjusting unit.

2. The method of claim 1, further comprising allowing the gas sensor to stabilize at a temperature of the fluid, and after the temperature of the gas sensor has stabilized at the temperature of the fluid, recording the temperature of the gas sensor.

3. The method of claim 2, wherein step ii) comprises: adjusting the temperature of the gas sensor to a substantially uniform predetermined temperature different from the temperature of the fluid using the first temperature adjusting unit, the second temperature adjusting unit, or both the first and second temperature adjusting units.

4. The method of claim 3, wherein in step c)ii) both the first temperature adjusting unit and the second temperature adjusting unit are used simultaneously to maintain the temperature of the gas sensor at the substantially uniform predetermined temperature.

5. The method of claim 1, further comprising the steps of: maintaining the temperature of the gas sensor with the first temperature adjusting unit, wherein the first temperature adjusting unit makes an adjustment having a first level of accuracy to the temperature of the gas sensor; and maintaining the temperature of the gas sensor with the second temperature adjusting unit, wherein the second temperature adjusting unit makes an adjustment having a second level of accuracy, wherein the first level of accuracy is greater than the second level of accuracy to the temperature of the gas sensor.

6. The method of claim 1, further comprising step iv) if the temperature of the gas sensor is below the predetermined temperature, heating the gas sensor with both the first and second temperature adjusting units.

7. A method of using an apparatus suitable for determining an amount of a gas in a fluid, the apparatus comprising:
   a) a gas sensor subassembly comprising a thermally conductive solid state material, the gas sensor subassembly having on the solid state material:
      i) a gas sensor adapted to sense an amount of a gas in a fluid when the gas sensor has a substantially uniform temperature;
      ii) a temperature sensor proximate to and coupled to the gas sensor for sensing the temperature of the gas sensor; and
      iii) a first temperature adjusting unit coupled to the gas sensor and adapted to adjust the temperature of the gas sensor only by heating;
   b) a second temperature adjusting unit located external to the gas sensor subassembly and adapted to adjust the temperature of the gas sensor by both heating and cooling; and
   c) a heat pipe coupling the second temperature adjusting unit to the gas sensor for directly controlling the temperature of the gas sensor;
   wherein the method comprises the steps of:
      i) detecting the temperature of the gas sensor with the temperature sensor;
      ii) adjusting the temperature of the gas sensor to a substantially uniform predetermined temperature different from the temperature of the fluid using the first temperature adjusting unit, the second temperature adjusting unit, or both the first and second temperature adjusting units;
      iii) if the temperature of the gas sensor is above the predetermined temperature, cooling the gas sensor with the second temperature adjusting unit; and
      iv) allowing the gas sensor to stabilize at the temperature of the fluid, and after the temperature of the gas sensor has stabilized at the temperature of the fluid, recording the temperature of the gas sensor.

8. The method of claim 7, wherein the substantially uniform predetermined temperature is higher than the temperature of the fluid.

9. The method of claim 7, wherein the substantially uniform predetermined temperature is lower than the temperature of the fluid.

10. The method of claim 7, wherein in step c)ii) both the first temperature adjusting unit and the second temperature adjusting unit are used simultaneously to maintain the temperature of the gas sensor at the substantially uniform predetermined temperature.

11. A system comprising:
   a) a gas sensor subassembly comprising a thermally conductive solid state material, the gas sensor subassembly having on the solid state material:
      i) a gas sensor adapted to sense an amount of a gas in a fluid when the gas sensor has a substantially uniform temperature;
      ii) a temperature sensor proximate to and coupled to the gas sensor for sensing the temperature of the gas sensor; and
      iii) a first temperature adjusting unit coupled to the gas sensor and adapted to adjust the temperature of the gas sensor only by heating;
   b) a second temperature adjusting unit separate from the gas sensor subassembly and adapted to adjust the temperature of the gas sensor by both heating and cooling;
   c) a heat pipe coupling the second temperature adjusting unit to the gas sensor for directly controlling the temperature of the gas sensor; and
   d) a controller coupled to the gas sensor, the temperature sensor, the first temperature adjusting unit and the second temperature adjusting unit, the controller adapted to when sensing the temperature of the gas sensor, if the temperature of the gas sensor is below a predetermined temperature, heating the gas sensor with the first temperature adjusting unit, the second temperature adjusting unit, or both the first and second temperature adjusting units to the predetermined temperature, or, if the temperature of the gas sensor is above the predetermined temperature, cooling the gas sensor with only the second temperature adjusting unit to the predetermined temperature.

12. The system of claim 11, wherein the controller is further adapted to: selectively disable the first temperature adjusting unit with a first temperature adjusting signal; selectively disable the second temperature adjusting unit with a second temperature adjusting signal; after the first temperature adjusting unit and the second temperature adjusting unit have been disabled, allow a temperature sensor signal to stabilize; and after the temperature sensor signal has stabilized, record data representing the temperature sensor signal to measure the temperature of the gas sensor.

13. The system of claim 11, wherein the controller is further adapted to: selectively adjust, with a first temperature adjusting signal, the temperature of the gas sensor to the substantially uniform temperature that is higher than a temperature of the fluid; and after selectively adjusting the temperature of the gas sensor to the substantially uniform temperature that is higher than the temperature of the fluid, record data representing a gas sensor signal to determine the amount of the gas in the fluid.

14. The system of claim 11, wherein the controller is further adapted to: selectively adjust, with a second temperature adjusting signal, the temperature of the gas sensor to the substantially uniform temperature that is higher than a temperature of the fluid; and after adjusting the temperature of the gas sensor to the substantially uniform temperature that is higher than the temperature of the fluid, record data representing a gas sensor signal to determine the amount of the gas in the fluid.

15. The system of claim 11, wherein the controller is further adapted to: selectively adjust, with a first temperature adjusting signal and a second temperature adjusting signal, the temperature of the gas sensor to the substantially uniform temperature that is higher than a temperature of the fluid; and after adjusting the temperature of the gas sensor to the substantially uniform temperature that is higher than the temperature of the fluid, record data representing a gas sensor signal to determine the amount of the gas in the fluid.

16. The system of claim 11, wherein the controller is further adapted to: selectively adjust, with a second temperature adjusting signal, the temperature of the gas sensor to the substantially uniform temperature that is lower than a temperature of the fluid; and after adjusting the temperature of the gas sensor to the substantially uniform temperature that is lower than the temperature of the fluid, record data representing a gas sensor signal to determine the amount of the gas in the fluid.

17. The system of claim 11, wherein the controller is further adapted to: selectively generate a first temperature adjusting signal to control the first temperature adjusting unit having a first level of accuracy; and selectively generate a second temperature adjusting signal to control the second temperature adjusting unit having a second level of accuracy, wherein the first level of accuracy is greater than the second level of accuracy in order to maintain the temperature of the gas sensor that is substantially uniform throughout the gas sensor.

18. A method of determining an amount of a gas in a fluid utilizing a system comprising:
  a) a gas sensor subassembly comprising a thermally conductive solid state material, the gas sensor subassembly having on the solid state material:
    i) a gas sensor adapted to sense an amount of a gas in a fluid when the gas sensor has a substantially uniform temperature;
    ii) a temperature sensor proximate to and coupled to the gas sensor for sensing the temperature of the gas sensor; and
    iii) a first temperature adjusting unit coupled to the gas sensor and adapted to adjust the temperature of the gas sensor only by heating;
  b) a second temperature adjusting unit separate from the gas sensor subassembly and adapted to adjust the temperature of the gas sensor by both heating and cooling;
  c) a heat pipe coupling the second temperature adjusting unit to the gas sensor for directly controlling the temperature of the gas sensor; and
  d) a controller coupled to the gas sensor, the temperature sensor, the first temperature adjusting unit and the second temperature adjusting unit, the controller adapted to when sensing the temperature of the gas sensor, if the temperature of the gas sensor is below a predetermined temperature, heating the gas sensor with the first temperature adjusting unit, the second temperature adjusting unit, or both the first and second temperature adjusting units to the predetermined temperature, or, if the temperature of the gas sensor is above the predetermined temperature, cooling the gas sensor with only the second temperature adjusting unit to the predetermined temperature;
  the method comprising the steps of:
  i) detecting the temperature of the gas sensor with the temperature sensor;
  ii) heating the gas sensor with the first temperature adjusting unit, the second temperature adjusting unit, or both the first and second temperature adjusting units when the detected temperature is below a predetermined temperature;
  iii) if the temperature of the gas sensor is below a predetermined temperature, heating the gas sensor with both the first and second temperature adjusting units; and
  iv) if the temperature of the gas sensor is above the predetermined temperature, cooling the gas sensor with the second temperature adjusting unit.

19. The method of claim 18, further comprising the steps of: selectively disabling the first temperature adjusting unit with a first temperature adjusting signal; selectively disabling the second temperature adjusting unit with a second temperature adjusting signal; after the first temperature adjusting unit and the second temperature adjusting unit have been disabled, allowing a temperature sensor signal to stabilize; and after the temperature sensor signal has stabilized, recording data representing the temperature sensor signal to measure the temperature of the gas sensor.

20. The method of claim 18, further comprising the steps of: selectively adjusting, with a first temperature adjusting signal, the temperature of the gas sensor to the substantially uniform temperature higher than a temperature of the fluid; and after selectively adjusting the temperature of the gas sensor to the substantially uniform temperature that is higher than the temperature of the fluid, recording data representing a gas sensor signal to determine the amount of the gas in the fluid.

21. The method of claim 18, further comprising the steps of: selectively adjusting, with a second temperature adjusting signal, the temperature of the gas sensor to the substantially uniform temperature that is higher than a temperature of the fluid; and after adjusting the temperature of the gas sensor to the substantially uniform temperature that is higher than the temperature of the fluid, record data representing a gas sensor signal to determine the amount of the gas in the fluid.

22. The method of claim 18, wherein step iii) comprises: selectively adjusting, with a first temperature adjusting signal and a second temperature adjusting signal, the temperature of the gas sensor to the substantially uniform temperature that is higher than a temperature of the fluid; and after adjusting the temperature of the gas sensor to the substantially uniform temperature that is higher than the temperature of the fluid, recording data representing a gas sensor signal to determine the amount of the gas in the fluid.

23. The method of claim 18, wherein step iv) comprises: selectively adjusting, with a second temperature adjusting signal, the temperature of the gas sensor to the substantially uniform temperature that is lower than a temperature of the fluid; and after adjusting the temperature of the gas sensor to the substantially uniform temperature that is lower than the temperature of the fluid, recording data representing a gas sensor signal to determine the amount of the gas in the fluid.

24. The method of claim 18, further comprising the steps of: selectively generating a first temperature adjusting signal to control the first temperature adjusting unit having a first level of accuracy; and selectively generating a second temperature adjusting signal to control the second temperature adjusting unit having a second level of accuracy, wherein the first level of accuracy is greater than the second level of accuracy in order to maintain the temperature of the gas sensor that is substantially uniform throughout the gas sensor.

* * * * *